United States Patent
Macchia et al.

(10) Patent No.: US 6,956,109 B1
(45) Date of Patent: Oct. 18, 2005

(54) CERAMIDE ANALOGS, PROCESS FOR THEIR PREPARATION AND THEIR USE AS ANTITUMOR AGENTS

(75) Inventors: Bruno Macchia, Pisa (IT); Aldo Balsamo, Lucca (IT); Marco Macchia, Livorno (IT); Mario Del Tacca, Pisa (IT); Romano Danesi, Livorno (IT)

(73) Assignee: Bracco S.p.A., Milan (IT)

( * ) Notice: Subject to any disclaimer, the term of this patent is extended or adjusted under 35 U.S.C. 154(b) by 84 days.

(21) Appl. No.: 10/031,692

(22) PCT Filed: Jul. 21, 2000

(86) PCT No.: PCT/EP00/07023

§ 371 (c)(1),
(2), (4) Date: Jan. 22, 2002

(87) PCT Pub. No.: WO01/07418

PCT Pub. Date: Feb. 1, 2001

(30) Foreign Application Priority Data

Jul. 22, 1999   (IT) ...................................... FI99A000169

(51) Int. Cl.⁷ .......................... C07G 11/00; C07G 3/00; C07H 15/00; C07H 17/00
(52) U.S. Cl. .......................... 536/4.1; 536/1.11; 514/23; 514/25; 514/27; 544/1; 544/224; 544/242
(58) Field of Search ........................... 544/1, 224, 242; 536/1.11, 4.1; 514/23, 25, 27

(56) References Cited

FOREIGN PATENT DOCUMENTS

| EP | 0 714 658 | | 6/1996 | |
|---|---|---|---|---|
| WO | WO 96/20710 | * | 7/1996 | .......... A61K/31/52 |
| WO | WO 98/52948 | * | 11/1998 | .......... C07D/473/02 |

OTHER PUBLICATIONS

Di Bussolo et al., "Direct Oxidative Glycoslations with Glycal Donors," J. Am,. Chem. Soc. 120:13515–13516, 1998.
Kinloch et al., "The Pharmacology of Apoptosis," Trends Pharm. Sci. 20:35–42, 1999.
Macchia et al., "Geranylgeranyl Diphosphate–Based Inhibitors of post–Translational Geranylgeraylation of Cellular Proteins," J. Med. Chem. 39:1352–1356, 1996.
Pless et al., "Boron Tris (trifluoroacetate) for Removal of Protecting Groups in Peptide Chemistry," Angew. Chem. Int. Ed. 12:147–148, 1973.
Talbot et al., "Synthesis of 4–Aminobutyric Acid and 2,4–Diaminobutyric Acid From Butyrolactone," Can. J. Chem. 36:593–596, 1958.
Sakai et al., "Ceramide Derivatives for Therapeutic Agents," Exp. Opin. Ther. Patents 8:1673–1682, 1998.

* cited by examiner

*Primary Examiner*—James O. Wilson
*Assistant Examiner*—Patrick Lewis
(74) *Attorney, Agent, or Firm*—Kramer, Levin, Naftalis & Frankel LLP

(57) ABSTRACT

The present invention is directed to ceramide analog compounds of general formula (I) the process for their preparation and use for the preparation of pharmaceutical formulations for the treatment of tumors.

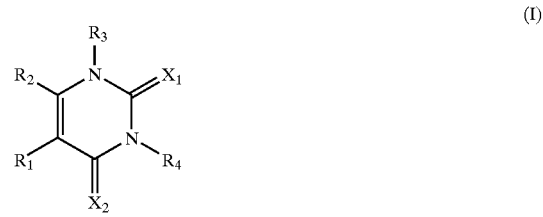

3 Claims, No Drawings

CERAMIDE ANALOGS, PROCESS FOR THEIR PREPARATION AND THEIR USE AS ANTITUMOR AGENTS

CROSS REFERENCE TO RELATED APPLICATIONS

This application claims priority under 35 U.S.C. § 371 to PCT Application PCT/EP00/07023, filed Jul. 21, 2000, which claims priority to Italian Patent Application No. FI99A000169, filed Jul. 22, 1999.

FIELD OF THE INVENTION

The present invention concerns the ceramide analog compounds of the general formula (I) specified below, their corresponding preparation process, and their use in the preparation of pharmaceutical formulations with an antitumor effect.

STATE OF THE ART

Ceramides are lipids composed of a fatty acid and sphingosine joined together by an amide link; they are generated by sphingomyelin, a sphingolipid occurring in the membranes of eukaryote cells due to the action of the enzyme sphingomyelinase, or they are synthesized by the action of the enzyme ceramide synthetase.

Sphingolipids such as sphingomyelin have always been considered as stable and metabolically inactive structural components of the membranes. It is only in the last decade that it has been demonstrated, instead, that sphingolipids have an active role in the mechanisms regulating cell response to exogenous stimuli, as well as in regulating cell growth, differentiation, transformation and adhesion.

It has also recently been demonstrated that the products of the demolition of sphingolipids, i.e. ceramides and sphingosine, play an important part in regulating the transmission mechanisms of the signals controlled by the membrane sphingolipids (Teruyuki Sakai et al., Exp Opin Ther Patents [1988] 8 [12]: 1673–1682). In particular, the distinctive characteristic of these products seems to be their involvement in the antiproliferative mechanisms of cell regulation, such as cell growth inhibition, the induction of cell differentiation and programmed cell death, or apoptosis.

Apoptosis has recently been the object of numerous studies (e.g. Ross A. Kinloch et al., TIPS, January 1999 [20]: 35–42), because this phenomenon lends itself to pharmacological "manipulation": in fact, a reduction in the frequency of the onset of cell apoptosis can have severe pathological consequences and facilitate tumor growth, hence the therapeutic potential of all those compounds that are capable of stimulating apoptosis.

From in-depth studies it has emerged that the ceramides in the cell membranes act as intracellular "effectors" of apoptosis, and therefore as potential inhibitors of tumor growth.

In order to boost this capacity of the endogenous ceramides pharmacologically, the ideal strategy seems to be to develop endogenous ceramide analogs that mimic their effects, are stable in relation to metabolization of the sphingosine ceramide and have an inhibitory effect on the ceramidase in order to prevent the generation of sphingosine, which represents a factor that stimulates proliferation, starting from the endogeneous sources of ceramides.

Such ceramide analogs should also have the capacity to penetrate the cell membrane.

There is consequent a need for ceramide analog compounds that are capable of crossing the cell membranes, penetrating inside the cells and mimicking the various properties of the ceramides, and particularly that of inducing apoptosis in human cancer cells.

SUMMARY OF THE INVENTION

The Applicant has now surprisingly discovered that the ceramide analog compounds of formula (I):

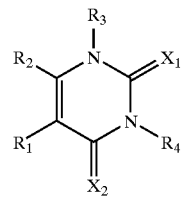

(I)

wherein:

$X_1$ and $X_2$ are selected between O and S;

$R_1$ and $R_2$ are selected between —$(CH_2)_{13}CH_3$ and alkyl or alkylene groups with from 2 to 6 carbon atoms, linear or branching, unsubstituted or substituted with one or more substituents selected among aromatic, primary, secondary and tertiary aminic, quaternary ammonium, carboxylic, hydroxylic, polyoxyalkylic and ethereal groups, aminoacids, halogen atoms or saccharidic portions, providing that between $R_1$ and $R_2$ only one is always —$(CH_2)_{13}CH_3$, $R_3$ and $R_4$ are selected between H and alkyl or alkylene groups with from 2 to 6 carbon atoms, linear or branching, unsubstituted or substituted with one or more substituents selected among aromatic, primary, secondary and tertiary aminic, quaternary ammonium, carboxylic, hydroxylic, polyoxyalkylic and ethereal groups, aminoacids, halogen atoms or saccharidic portions, are capable of penetrating inside the biological membranes and effectively inducing apoptosis of the cancer cells.

The compounds of the general formula (I) considered in the present invention have therefore proved suitable for the preparation of pharmaceutical formulations for the treatment of tumors.

The object of the present invention is therefore represented by the compounds of the general formula (I), their corresponding preparation process, and their use in the preparation of pharmaceutical formulations for use in the treatment of tumors.

The characteristics and advantages of the compounds of the general formula (I) according to the present invention will be illustrated in detail in the following description.

DETAILED DESCRIPTION OF THE INVENTION

The present invention refers to the compounds of the general formula (I), as defined above. Said compounds (I) have proved capable of penetrating inside the biological membranes and effectively inducing the apoptosis of cancer cells. The following compounds have proved particularly effective and highly cytotoxic:

compound of formula (I) where $X_1=S$, $X_2=O$, $R_1=$—$(CH_2)_{13}CH_3$, $R_2$=ethyl, and $R_3=R_4=H$ [compound (3)];

compound of formula (I) where $X_1=X_2=O$, $R_1=$—$(CH_2)_{13}CH_3$, $R_2$=ethyl, and $R_3=R_4=H$ [compound (4)];

compound of formula (I) where $X_1=X_2=O$, $R_1=-(CH_2)_{13}CH_3$, $R_2$=n-propyl, and $R_3=R_4=H$ [compound (6)];

compound of formula (I) where $X_1=X_2=O$, $R_1=-(CH_2)_{13}CH_3$, $R_2$=i-butyl, and $R_3=R_4=H$ [compound (10)];

The present compounds of formula (I) can be conveniently prepared by processes well known in the art. For example, a process for the preparation of the present compounds of formula (I) wherein $R_3=R_4=H$ includes the following steps:

i) reaction of the ethyl ester (II) with acid chloride (III) to obtain the β-ketoester of formula (IV):

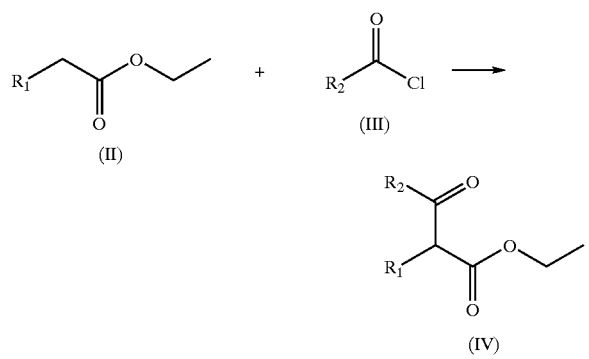

ii) reaction of the β-ketoester of formula (IV) with thiourea (V) to obtain the compound of formula (I) where $X_1=S$, $X_2=O$:

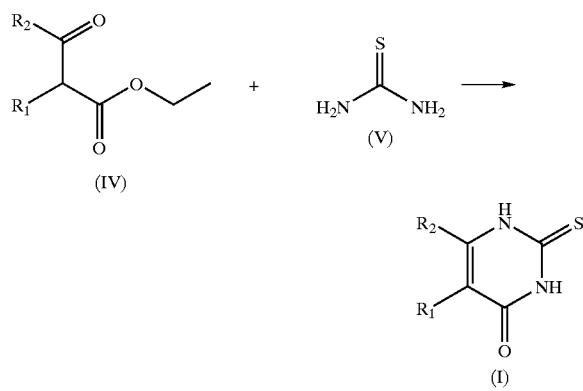

iii) reaction compound of formula (I) where $X_1=S$, $X_2=O$, with refluxed chloroacetic acid to obtain the compound of formula (I) wherein $X_1=X_2=O$:

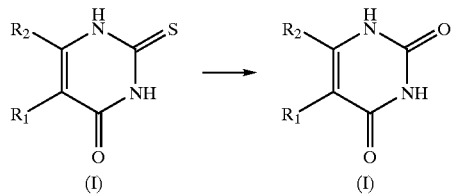

wherein $X_1$, $X_2$, $R_1$ and $R_2$ have above-specified meanings.

Step i) of the said process is generally carried out in an organic solvent, such as THF, at a temperature of 0° C. Said reaction is preferably carried out in an inert gas atmosphere.

The reaction product of formula (IV) can be recovered from the reaction mixture by addition of a saturated $NH_4Cl$ solution and subsequent extraction with diethyl ether.

Step ii) of the present process is carried out by means of the addition of thiourea in ethanol and sodium ethoxide on the raw reaction product coming from step i), without the need for any purification. In step ii) temperature is preferably maintained around 90° C. The reaction product is generally recovered from the reaction mixture by acidification at pH 2, e.g. by adding conc. HCl, and filtration of the resulting precipitate, which can be purified, if necessary, by washing with acetone.

The reaction product obtained in step ii) can be further purified by chromatography on silica gel, preferably using a mixture of ethyl acetate and petroleum ether in proportions of 2:1 as an eluant.

Step iii) of the process according to the above procedure is generally carried out by adding chloroacetic acid to the product coming from step ii), e.g. in the form of a 10% aqueous solution, and reflux heated. The crude residue thus obtained can then be purified by washing with absolute ethanol and then with diethyl ether.

The product coming from step iii) can be further purified by chromatography on silica gel, preferably using a mixture of ethyl acetate and hexane in proportions of 1:2 as an eluant.

The present compounds of formula (I) wherein $R_3$ and/or $R_4$ are different from H, can be prepared from the β-ketoester of formula (IV) or from the compounds of formula (I) wherein $R_3=R_4=H$, obtained for example as explained above, by means of well-known processes.

Other processes for the preparation of the present formula (I) compounds are disclosed in the examples.

The compounds of formula (I) according to the present invention can be formulated with pharmaceutically acceptable excipients and/or diluents in order to prepare pharmaceutical formulations suitable for the treatment of tumor pathologies.

The following examples are given as a partial illustration of the present invention.

EXAMPLE 1

Preparation of the compound of formula (I) where $X_1=S$, $X_2=O$, $R_2=-(CH_2)_{13}CH_3$, $R_1$=ethyl, and $R_3=R_4=H$ [compound (1)]

A solution prepared by dissolving 0.37 g of ethyl butyrate in 2 ml of anhydrous tetrahydrofuran (THF) is added drop by drop, at a temperature of 0° C. and in an argon gas atmosphere, to 1.9 ml of a 2M solution of lithiodiisopropylamine (LDA) in anhydrous THF. After 30 minutes of agitation at 0° C., the reaction mixture is added to a solution obtained by dissolving 1 g of pentadecanol chloride (3.8 mmol) in 5 ml of anhydrous THF, previously cooled to 0° C. The resulting mixture is constantly agitated at room temperature for 12 hours, then added to a saturated solution of $NH_4Cl$. The organic phase is separated from the aqueous phase, then extracted with diethyl ether. The organic extracts are combined, washed with a saturated aqueous solution of NaCl, dried with anhydrous $Na_2SO_4$ and then evaporated until dry to provide a crude residue (1.20 g) composed almost exclusively of β-ketoester (IV) where $R_2=-(CH_2)_{13}CH_3$ and $R_1$=ethyl. [$^1$H-NMR (CDCl$_3$, 200 MHz) δ 0.83–0.94 (m, 6H), 1.07 (t, 3H, J=7.4 Hz), 1.15–1.36 (m, 24H), 1.81–2.02 (m, 2H), 2.11–2.57 (m, 2H), 3.34 (t, 1H, J=7.3 Hz), 4.15 (q, 2H, J=7.3 Hz). MS m/e 340 M$^+$].

The resulting crude residue (1.20 g) containing the β-ketoester (IV) where $R_2=-(CH_2)_{13}CH_3$ and $R_1$=ethyl, is dissolved in 20 ml of absolute ethanol and then added to 3.61 g of thiourea (47.5 mmol) and 6.47 g of sodium ethoxide (95.1 mmol). The mixture is agitated for 60 minutes at 90°

C. After cooling to room temperature, the reaction mixture is filtered and the filtrate is evaporated until dry; the residue thus obtained is then restored with a mixture of water and THF in proportions of 10:1 until it has become completely soluble. The solution, cooled to 0° C., is acidified to pH 2 with conc. HCl; the precipitate that develops is filtered and washed with small quantities of acetone and provides a crude residue that is purified by chromatography on silica gel using ethyl acetate and petroleum ether in proportions of 2:1 as an eluant, finally obtaining 290 mg (0.82 mmol; yield=26%) of the required compound of formula (I) (m.p.= 167–169° C.; [$^1$H-NMR (CDCl$_3$, 200 MHz) δ 0.89 (t, 3H, J=6.2 Hz), 1.09 (t, 3H, J=7.4 Hz), 1.17–1.36 (m, 24H), 2.34–2.49 (m, 4H), 8.88 (br, 1H, D$_2$O exchangeable), 9.81 (br, 1H, D$_2$O exchangeable); MS m/e 352 M$^+$).

EXAMPLE 2

Preparation of the compound of formula (I) where $X_1=X_2=O$, $R_2=-(CH_2)_{13}CH_3$, $R_1$=ethyl, and $R_3=R_4=H$ [compound (2)]

160 mg (0.45 mmol) of the product (1) obtained as described in Example 1 are added to 11.4 ml of a 10% aqueous solution of chloroacetic acid and the mixture thus obtained is reflux heated for 12 hours. The resulting precipitate is then filtered, washed first with absolute ethanol, then with diethyl ether, to obtain a crude residue that, after purification by chromatography on silica gel using a mixture of ethyl acetate and hexane in proportions of 1:2 as an eluant, gave rise to 48 mg (0.14 mmol, yield=32%) of the required pure compound (m.p.=132–134° C.; [$^1$H-NMR (CDCl$_3$, 200 MHz) δ 0.87 (t, 3H, J=6.2 Hz), 1.06 (t, 3H, J=7.4 Hz), 1.15–1.36 (m, 24H), 2.31–2.49 (m, 4H), 9.06 (br, 1H, D$_2$O exchangeable), 9.89 (br, 1H, D$_2$O exchangeable); MS m/e 336 M$^+$).

EXAMPLE 3

Preparation of the compound of formula (I) wherein $X_1=S$, $X_2=O$, $R_1=-(CH_2)_{13}CH_3$, $R_2$=ethyl, and $R_3=R_4=H$ [compound (3)]

A solution obtained by dissolving 1 g of ethyl palmitate (3.52 mmol) in 3 ml of anhydrous THF is added drop by drop, at a temperature of 0° C. in an argon gas atmosphere, to 2.1 ml of a 2M solution of lithiodiisopropylamine (LDA) in anhydrous THF. After 30 minutes of agitation at 0° C., the reaction mixture is added to a solution obtained by dissolving 2.39 g (4.23 mmol) of propionyl chloride in 5 ml of anhydrous THF. The resulting mixture is constantly agitated at room temperature for 12 hours, then added to a saturated solution of NH$_4$Cl. The organic phase is separated from the aqueous phase, then extracted with diethyl ether. The organic extracts are combined, washed with a saturated aqueous solution of NaCl, dried with anhydrous Na$_2$SO$_4$ and then evaporated until dry to provide a crude residue (1.31 g) composed almost exclusively of β-ketoester (IV) where $R_1=-(CH_2)_{13}CH_3$ and $R_2$=ethyl. [$^1$H-NMR (CDCl$_3$, 200 MHz) δ 0.79–0.92 (m, 6H), 1.11 (t, 3H, J=7.6 Hz), 1.17–1.39 (m, 24H), 1.48–1.62 (m, 2H), 2.26 (q, 2H, J=7.6 Hz), 3.36 (t, 1H, J=7.3 Hz), 4.15 (q, 2H, J=7.2 Hz); MS m/e 340 M$^+$].

1.31 g of the resulting crude residue containing the β-ketoester (IV) where $R_1=-(CH_2)_{13}CH_3$ and $R_2$=ethyl, is dissolved in 20 ml of absolute ethanol and then added to 4.01 g of thiourea (52.8 mmol) and 7.18 g of sodium ethoxide (105.6 mmol). The mixture is agitated for 60 minutes at 90° C. After cooling to room temperature, the reaction mixture is filtered and the filtrate is evaporated until dry; the residue thus obtained is then treated with a mixture of water and THF in proportions of 10:1 until it has become completely soluble. The solution is cooled to 0° C. and acidified to pH 2 with conc. HCl; the precipitate that develops due to acidification is filtered and washed with small quantities of acetone and provides a crude residue that is purified by chromatography on silica gel using ethyl acetate and petroleum ether in proportions of 2:1 as an eluant, finally obtaining 310 mg (0.88 mmol; yield=25%) of a product that coincides with the required pure compound 3 (m.p.= 100–102° C.; [$^1$H-NMR (CDCl$_3$, 200 MHz) δ 0.88 (t, 3H, J=6.4 Hz), 1.01 (t, 3H, J=7.4 Hz), 1.18–1.38 (m, 24H), 2.35 (t, 2H, J=7.4 Hz), 2.48 (q, 2H, J=7.6 Hz), 9.08 (br, 1H, D$_2$O exchangeable), 9.73 (br, 1H, D$_2$O exchangeable); MS m/e 352 M$^+$).

EXAMPLE 4

Preparation of the compound of formula (I) wherein $X_1=X_2=O$, $R_1=-(CH_2)_{13}CH_3$, $R_2$=ethyl, and $R_3=R_4=H$ [compound (4)]

160 mg (0.45 mmol) of the compound (3) obtained as described in Example 3 are added to 11.4 ml of a 10% aqueous solution of chloroacetic acid and the mixture thus obtained is reflux heated for 12 hours. The resulting precipitate is then filtered, washed first with absolute ethanol, then with diethyl ether, to obtain a crude residue that, after purification by chromatography on silica gel using a mixture of ethyl acetate and hexane in proportions of 1:2 as an eluant, gave rise to 57 mg (0.17 mmol, yield=38%) of the compound (4) (m.p.=110–112° C.; [$^1$H-NMR (CDCl$_3$, 200 MHz) δ 0.89 (t, 3H, J=6.4 Hz), 1.02 (t, 3H, J=7.4 Hz), 1.12–1.42 (m, 24H), 2.34 (t, 2H, J=7.2 Hz), 2.49 (q, 2H, J=7.6 Hz), 9.15 (br, 1H, D$_2$O exchangeable), 9.53 (br, 1H, D$_2$O exchangeable); MS m/e 336 M$^+$).

EXAMPLE 5

Preparation of the compound of formula (I) wherein $X_1=S$, $X_2=O$, $R_1=-(CH_2)_{13}CH_3$, $R_2$=n-propyl, and $R_3=R_4=H$ [compound (5)]

Compound (5) was prepared following a procedure similar to the one described in Example 3, obtaining a product which resulted in: MS m/e 366 M$^+$.

EXAMPLE 6

Preparation of the compound of formula (I) wherein $X_1=X_2=O$, $R_1=-(CH_2)_{13}CH_3$, $R_2$=n-propyl, and $R_3=R_4=H$ [compound (6)]

Compound (6) was prepared following a procedure similar to the one described in Example 4, obtaining a product which resulted in: MS m/e 350 M$^+$.

EXAMPLE 7

Preparation of the compound of formula (I) wherein $X_1=S$, $X_2=O$, $R_1=-(CH_2)_{13}CH_3$, $R_2$=n-butyl, and $R_3=R_4=H$ [compound (7)]

Compound (7) was prepared following a procedure similar to the one described in Example 3, obtaining a product which resulted in: MS m/e 380 M$^+$.

EXAMPLE 8

Preparation of the compound of formula (I) wherein $X_1=X_2=O$, $R_1=-(CH_2)_{13}CH_3$, $R_2$=n-butyl, and $R_3=R_4=H$ [compound (8)]

Compound (8) was prepared following a procedure similar to the one described in Example 4, obtaining a product which resulted in: MS m/e 364 M$^+$.

EXAMPLE 9

Preparation of the compound of formula (I) wherein $X_1=S$, $X_2=O$, $R_1=—(CH_2)_{13}CH_3$, $R_2=$i-butyl, and $R_3=R_4=H$ [compound (9)]

Compound (9) was prepared following a procedure similar to the one described in Example 3, obtaining a product which resulted in: MS m/e 380 M$^+$.

EXAMPLE 10

Preparation of the compound of formula (I) wherein $X_1=X_2=O$, $R_1=—(CH_2)_{13}CH_3$, $R_2=$i-butyl, and $R_3=R_4=H$ [compound (10)]

Compound (10) was prepared following a procedure similar to the one described in Example 4, obtaining a product which resulted in: MS m/e 364 M$^+$.

EXAMPLE 11

Preparation of the compound of formula (I) wherein $X_1=S$, $X_2=O$, $R_1=—(CH_2)_{13}CH_3$, $R_2=$neopentyl, and $R_3=R_4=H$ [compound (11)]

Compound (11) was prepared following a procedure similar to the one described in Example 3, obtaining a product which resulted in: MS m/e 394 M$^+$.

EXAMPLE 12

Preparation of the compound of formula (I) wherein $X_1=X_2=O$, $R_1=—(CH_2)_{13}CH_3$, $R_2=$neopentyl, and $R_3=R_4=H$ [compound (12)]

Compound (12) was prepared following a procedure similar to the one described in Example 4, obtaining a product which resulted in: MS m/e 378 M$^+$.

EXAMPLE 13

Preparation of the compound of formula (I) wherein $X_1=S$, $X_2=O$, $R_1=—(CH_2)_{13}CH_3$, $R_2=$2-phenyl-ethyl, and $R_3=R_4=H$ [compound (13)]

Compound (13) was prepared following a procedure similar to the one described in Example 3, obtaining a product which resulted in: MS m/e 428 M$^+$.

EXAMPLE 14

Preparation of the compound of formula (I) wherein $X_1=X_2=O$, $R_1=—(CH_2)_{13}CH_3$, $R_2=$2-phenyl-ethyl, and $R_3=R_4=H$ [compound (14)]

Compound (14) was prepared following a procedure similar to the one described in Example 4, obtaining a product which resulted in: MS m/e 412 M$^+$.

EXAMPLE 15

Preparation of the compound of formula (I) wherein $X_1=S$, $X_2=O$, $R_1=—(CH_2)_{13}CH_3$, $R_2=—(CH_2)_3NH_2$ and $R_3=R_4=H$ [compound (15)]

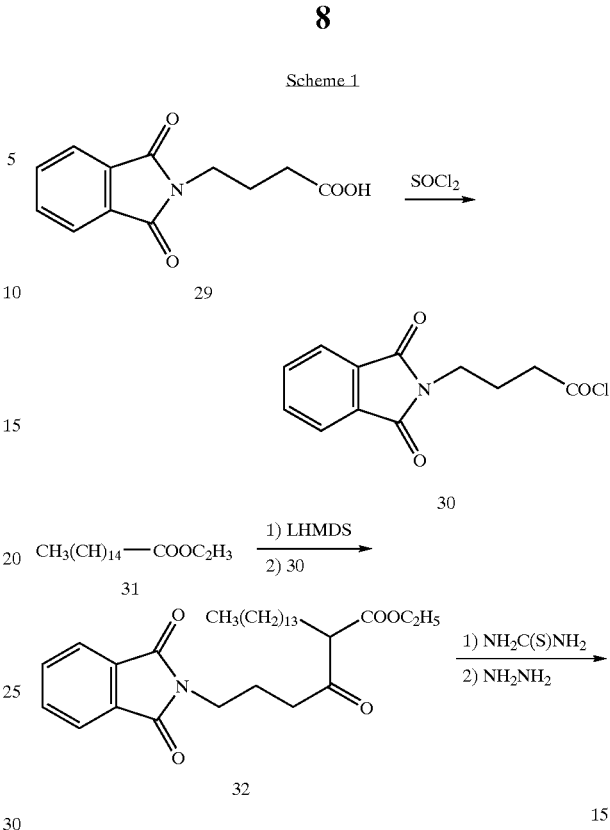

Scheme 1

Compound (15) was prepared following the procedure described in the above Scheme 1.

Synthesis of β-ketoester (32). 2.4 g (10 mmol) of 4-phthalimidoburyric acid (29) (prepared as described in G. Talbot, R. Gaudry, L. Berlinguet *Can. J. Chem.* 1958, 36, 593–596) was dissolved in 7.5 ml of SOCl$_2$ and the mixture was refluxed under nitrogen for 3 hours. Excess of SOCl$_2$ was then removed under a nitrogen flow and the resulting acid chloride (30) was used in the next step without further purification. Separately, a solution of ethyl palmitate (31) (1.47 g, 5.16 mmol) in anhydrous THF (6.5 ml) was slowly added to a 1.0 M solution of lithium bis(trimethylsilyl)amide (LHMDS) in THF (6.2 ml, 6.2 mmol) cooled at −20° C. and the resulting mixture was stirred for additional 20 minutes. Acid chloride (30) previously prepared as described above, was dissolved in anhydrous THF (10 ml), cooled at −20° C., and added via cannula to the solution containing (31) and LHMDS at the same temperature. The mixture was stirred at −20° C. for 30 minutes and then at room temperature for 2 hours. The reaction was quenched with a saturated aqueous solution of ammonium chloride and extracted with ethyl acetate. The organic layer was dried over sodium sulfate and concentrated under vacuum. The crude residue was purified by silica gel column chromatography using hexane-ethyl acetate (8:2) as the eluant, to obtain 0.95 g (1.9 mmol, 37% yield) of pure β-ketoester (32) as a colorless oil: $^1$H NMR (CDCl$_3$, 200 MHz) δ 0.87 (t, 3H, J=6.4 Hz), 1.23 (t, 3H, J=7.3 Hz), 1.24 (bs, 24H), 2.05 (quintet, 2H, J=7.2 Hz), 2.24–2.34 (m, 4H), 2.51 (t, 2H, J=7.6 Hz), 3.78 (t, 1H, J=6.9 Hz), 4.12 (q, 2H, J=7.1 Hz), 7.69–7.73 (m, 2H), 7.82–7.87 (m, 2H); MS (FAB$^+$) m/z 500 (M+H)$^+$.

Synthesis of thiouracil (15). β-Ketoester (32) (0.12 g, 0.24 mmol) was dissolved in 2 ml of absolute ethanol. Thiourea (0.024 g, 0.33 mmol) and potassium t-butoxyde (0.028 g, 0.25 mmol) were added and the resulting mixture was refluxed for 5 hours. The mixture was then cooled to room temperature and the solvent was removed under vacuum. The residue was treated with 20 ml of water and neutralized with an aqueous solution of acetic acid 0.5 N. The product was extracted with ethyl acetate and the organic layer was washed with brine, dried over anhydrous sodium sulfate and concentrated under vacuum. The crude residue was then redissolved in 3 ml of ethanol, treated with 0.06 ml of hydrazine monohydrate (1.3 mmol), and the mixture was refluxed overnight. The resulting suspension was cooled to room temperature. The white solid was collected by filtration, washed with small portions of ethyl acetate, and dried under vacuum, to give 51 mg (0.13 mmol, 54% yield) of product (15): m.p. 123–125° C.; $^1$H NMR (CDCl$_3$, 200 MHz) δ 0.88 (t, 3H, J=6.4 Hz), 1.26 (bs, 24H), 1.77 (m, 2H), 2.29–2.45 (m, 6H), 8.87 (bs, 1H), 9.19 (bs, 1H); MS (FAB$^+$) m/z 381 (M+H)$^+$.

EXAMPLE 16

Preparation of the compound of formula (I) where $X_1$=S, $X_2$=O, $R_1$=—(CH$_2$)$_{13}$CH$_3$, $R_2$=—(CH$_2$)$_3$OSiPh$_2$t-Bu and $R_3$=$R_4$=H [compound (16)]

Compound (16) was prepared following the procedure described in the following Scheme 2

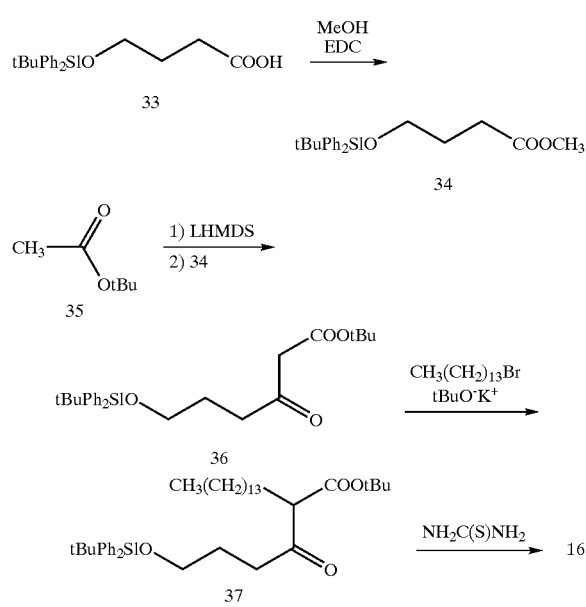

Synthesis of methyl ester (34). A solution of acid (33) (1.15 g, 3.36 mmol) (prepared as in: A. G. M. Barrett, J. A. Flygare J. Org. Chem. 1991, 56, 638–642) in methanol (25 ml) was treated with 1.62 g (8.44 mmol) of 1-[3-(dimethylamino)propyl]-3-ethylcarbodiimide hydrochloride (EDC). The resulting solution was stirred under nitrogen at room temperature for 3.5 hours. The solvent is then removed under vacuum and the residue was diluted with chloroform (100 ml) and water (50 ml). The organic layer was washed with brine, dried over sodium sulfate and concentrated under vacuum. The crude residue was purified by silica gel column chromatography using hexane-ethyl acetate (9:1) as the eluant, to obtain 0.59 g (1.6 mmol, 49% yield) of pure ester (34) as a colorless oil: $^1$H NMR (CDCl$_3$, 200 MHz) δ 1.05 (s, 9H), 1.88 (tt, 2H, J=7.7, 5.9 Hz), 2.47 (t, 2H, J=7.5 Hz), 3.66 (s, 3H), 3.68 (t, 2H, J=6.0 Hz), 7.37–7.42 (m, 6H), 7.63–7.68 (m, 4H).

Synthesis of β-ketoester (36). A solution of t-butyl acetate (35) (4.24 g, 36.5 mmol) in anhydrous THF (40 ml) previously cooled at −78° C. was added drop by drop via cannula under argon to a 1M solution of LHMDS in THF (51.5 ml, 51.5 mmol). To the resulting solution, previously stirred at the same temperature for 30 minutes, was added drop by drop via cannula another solution of methyl ester (34) (4.07 g, 11.4 mmol) in anhydrous THF (20 ml) at −78° C. The reaction mixture was stirred under argon for 20 minutes at the same temperature, and then 3 more hours at room temperature. The reaction was quenched with 400 ml of saturated aqueous solution of ammonium chloride and extracted with diethyl ether (2×300 ml). The organic layer was dried over anhydrous sodium sulfate and concentrated under vacuum. The crude residue was purified by silica gel column chromatography using hexane-diethyl ether (8:2) as the eluant, to obtain 2.8 g (6.4 mmol, 56% yield) of pure β-ketoester (36) as a colorless oil: $^1$H NMR (CDCl$_3$, 200 MHz) δ 1.04 (s, 9H), 1.46 (s, 9H), 1.85 (quintet, 2H, J=6.7 Hz), 2.66 (t, 2H, J=7.3 Hz), 3.34 (s, 2H), 3.67 (t, 2H, J=6.0 Hz), 7.37–7.43 (m, 6H), 7.62–7.67 (m, 4H); MS (FAB$^+$) m/z 441 (M+H)$^+$, 385 (M+H-isobutene)$^+$.

Synthesis of alkylated β-ketoester (37). A solution of β-ketoester (36) (2.79 g, 6.34 mmol) in anhydrous 1,2-dimethoxyethane (DME) (17 ml) was added to a solution of potassium tert-butoxide (0.85 g, 6.97 mmol) in anhydrous DME (7 ml). The resulting solution was stirred at room temperature for 20 minutes, after which time 1.7 ml (1.6 g, 5.7 mmol) of 1-bromotetradecane were added. The reaction mixture was stirred at 80° C. for 2 hours. The reaction was quenched with 150 ml of a saturated aqueous solution of ammonium chloride and extracted with diethylether (2×300 ml). The organic layer was washed with brine, dried over sodium sulfate and concentrated under vacuum. The crude residue was purified by silica gel column chromatography using hexane-diethyl ether (9:1) as the eluant, to obtain 1.16 g (1.82 mmol, 32% yield) of pure mono-alkylated product (37) as a colorless oil: $^1$H NMR (CDCl$_3$, 200 MHz) δ 0.88 (t, 3H, J=6.2 Hz), 1.04 (s, 9H), 1.25 (bs, 24H), 1.43 (s, 9H), 1.76–1.89 (m, 4H), 2.64 (td, 2H, J=7.3, 4.4 Hz), 3.13 (t, 1H, J=7.3 Hz), 3.66 (t, 2H, J=6.0 Hz), 7.34–7.43 (m, 6H), 7.62–7.67 (m, 4H); MS (FAB$^+$) m/z 581 (M+H-isobutene)$^+$, 563 (M-tBuO)$^+$.

Synthesis of thiouracil (16). A solution containing alkylated β-ketoester (37) (1.16 g, 1.82 mmol) in absolute ethanol (24 ml) in a screw-cap sealed vial was treated first with 0.19 g (2.6 mmol) of thiourea and then with 0.25 g (2.0 mmol) of potassium tert-butoxide. The resulting solution was stirred at 100° C. for 6 hours. The solvent was then removed under vacuum. The residue was diluted with water and neutralized to pH=6–7 with 0.5 N acetic acid. The product was extracted with ethyl acetate. The organic layer was washed with brine, dried over anhydrous sodium sulfate and concentrated under vacuum. The crude residue was purified by silica gel column chromatography using hexane-diethyl ether (8:2) as the eluant, to obtain 0.52 g (0.84 mmol, 46% yield) of pure thiouracil product (16) as a colorless oil: $^1$H NMR (CDCl$_3$, 200 MHz) δ 0.87 (t, 3H, J=6.2 Hz), 1.10 (s, 9H), 1.24 (bs, 24H), 1.74 (quintet, 2H, J=6.8 Hz), 2.34 (t, 2H, J=7.4 Hz), 2.60 (t, 2H, J=7.5 Hz), 3.74 (t, 2H, J=5.8 Hz), 7.40–7.46 (m, 6H), 7.66–7.70 (m, 4H), 9.29 (bs, 1H), 9.55 (bs, 1H); MS (FAB$^+$) m/z 547 (M+H—NHC(S)NH)$^+$.

EXAMPLE 17

Preparation of the compound of formula (I) where $X_1$=S, $X_2$=O, $R_1$=—(CH$_2$)$_{13}$CH$_3$, $R_2$=—(CH$_2$)$_3$OH and $R_3$=$R_4$=H [compound (17)]

Scheme 3

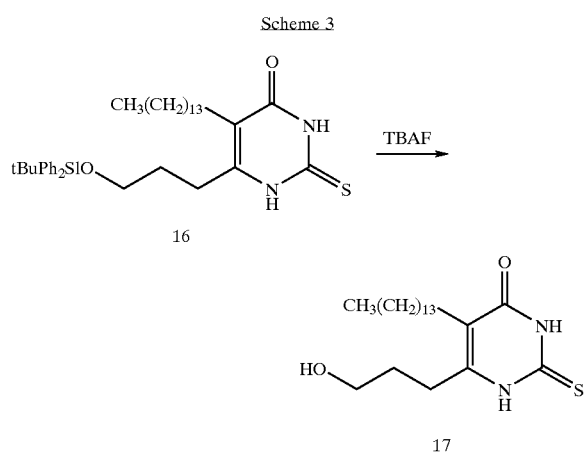

According to the above Scheme 3 the silyl ether 16 (0.16 g, 0.26 mmol) was treated with 0.8 ml of a 1M solution of tetrabutylammonium fluoride (TBAF) in THF (0.8 mmol) under argon at room temperature for 2 hours. The solvent was then removed under vacuum and the residue was extracted with ethyl acetate. The organic layer was washed with brine, dried over sodium sulfate and concentrated under vacuum. The crude residue was purified by silica gel column chromatography using hexane-ethyl acetate (1:1) as the eluant, to obtain 0.079 g (0.21 mmol, 81% yield) of pure deprotected alcohol (17) as a white solid: m.p. 128–130° C.; $^1$H NMR (CDCl$_3$, 200 MHz) δ 0.88 (t, 3H, J=6.7 Hz), 1.25 (bs, 24H), 1.91 (quintet, 2H, J=6.1 Hz), 2.37 (pseudo t, 2H, J=7.4 Hz), 2.67 (pseudo t, 2H, J=6.3 Hz), 3.84 (t, 2H, J=5.6 Hz), 9.16 (bs, 1H), 10.52 (bs, 1H); MS (EI; 70 eV) m/z 382 (M)$^+$, 365 (M—OH)$^+$, 323 (M—NHC=S)$^+$.

EXAMPLE 18

Preparation of the compound of formula (I) where X$_1$=S, X$_2$=O, R$_1$=—(CH$_2$)$_{13}$CH$_3$, R$_2$=—(CH$_2$)$_3$OC(O)CH$_2$NH-Cbz and R$_3$=R$_4$=H [compound (18)]

Scheme 4

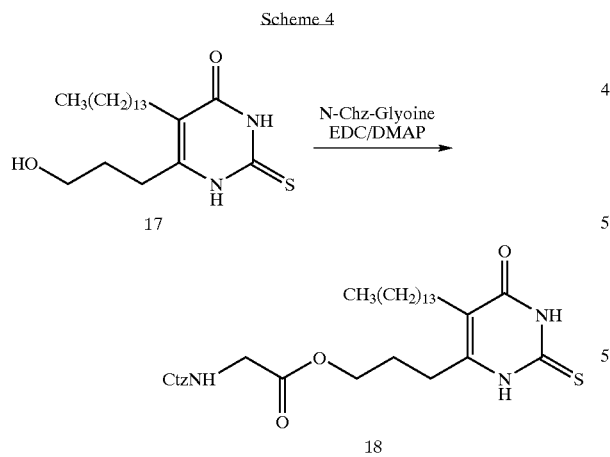

According to scheme 4 a solution of the alcohol (17) (0.038 g, 0.099 mmol) in anhydrous THF (2.5 ml) was sequentially treated with 0.031 g (0.15 mmol) of N-carbobenzyloxyglycine (N-Cbz-Gly), 0.034 g (0.18 mmol) of 1-[3-(dimethylamino)propyl]-3-ethylcarbodiimide hydrochloride (EDC), and 0.0012 g (0.0096 mmol) of 4-(dimethylamino)pyridine (DMAP). The mixture was stirred at room temperature for 5 hours under argon. The solvent was removed under vacuum and the residue was purified by silica gel column chromatography using hexane-ethyl acetate (1:1) as the eluant, to obtain 0.052 g (0.091 mmol, 92% yield) of product (18) as a thick syrup: $^1$H NMR (CDCl$_3$, 200 MHz) δ 0.87 (t, 3H, J=6.6 Hz), 1.25 (bs, 24H), 1.91 (m, 2H), 2.31 (t, 2H, J=7.7 Hz), 2.47 (t, 2H, J=7.7 Hz), 4.07 (d, 2H, J=5.9 Hz), 4.27 (t, 2H, J=5.2 Hz), 5.24 (s, 2H), 5.52 (t, 1H, J=5.8 Hz), 7.31–7.38 (m, 5H), 10.09 (bs, 1H), 10.85 (bs 1H); MS (FAB$^+$) m/z 574 (M+H)$^+$, 532 (M—C(S)+H)$^+$.

EXAMPLE 19

Preparation of the compound of formula (I) where X$_1$=S, X$_2$=O, R$_1$=—(CH$_2$)$_{13}$CH$_3$, R$_2$=—(CH$_2$)$_3$OC(O)CH$_2$NH$_2$ and R$_3$=R$_4$=H [compound (19)]

Scheme 5

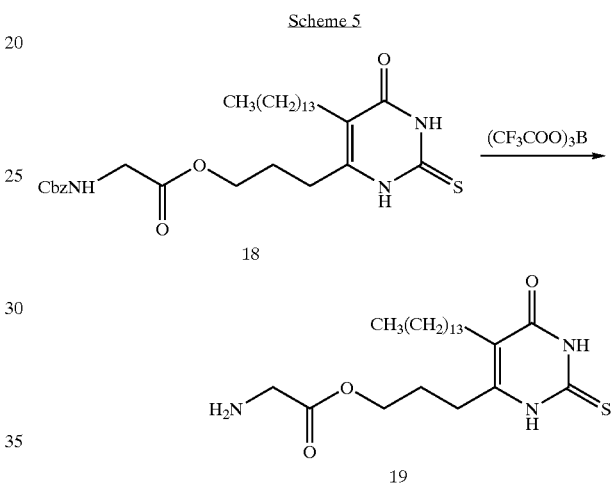

According to the above scheme 5 a solution of Cbz-protected compound (18) (0.032 g, 0.055 mmol) in trifluoroacetic acid (1 ml) as treated with 0.22 mmol of freshly prepared boron tris(trifluoroacetate) (prepared as reported in: J. Pless, W. Bauer *Angew. Chem. Int. Ed.* 1973, 12, 147–148) at 0° C. under argon. The mixture was stirred for 1 hour at the same temperature and overnight at room temperature. The solvent was removed under vacuum and the residue was purified by silica gel column chromatography using a mixture dichloromethane:acetone 7:3 as the eluant, to obtain 0.020 g (0.045 mmol, 82% yield) of product (19) as a thick syrup: $^1$H NMR (CDCl$_3$, 200 MHz) δ 0.87 (t, 3H, J=6.4 Hz), 1.25 (bs, 24H), 1.72 (m, 2H), 2.32 (m, 2H), 2.63 (m, 2H), 3.61 (t, 2H, J=7.0 Hz), 4.30 (t, 2H, J=6.6 Hz); MS (FAB$^+$) m/z 365 (M—NHC(S)NH)$^+$.

EXAMPLE 20

Preparation of the compound of formula (I) where X$_1$=S, X$_2$=O, R$_1$=—(CH$_2$)$_{13}$CH$_3$, R$_2$ = 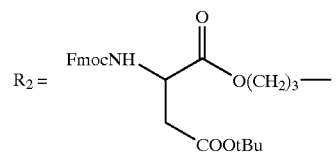

and $R_3=R_4=H$ [compound (20)]

Scheme 6

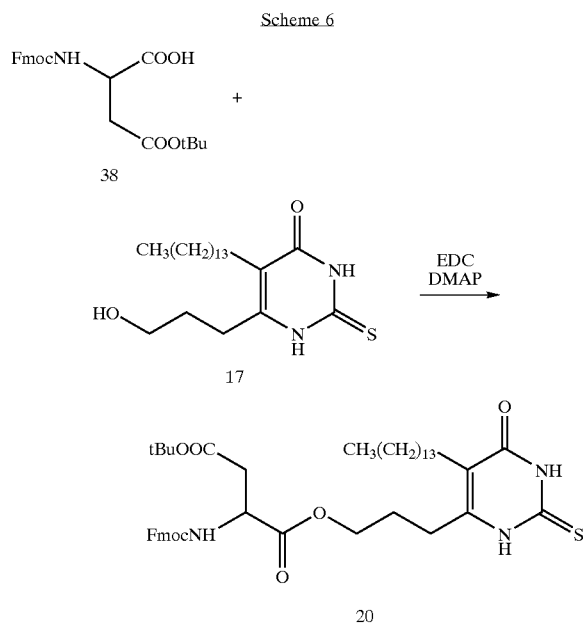

According to the above scheme 6 a solution of alcohol (17) (0.120 g, 0.314 mmol) in anhydrous THF (10 ml) was treated sequentially with N-(9-Fluorenylmethoxycarbonyl)-L-aspartic acid tert-butyl ester (38) (0.194 g, 0.471 mmol), 1-[3-(dimethylamino)propyl]-3-ethylcarbodiimide hydrochloride (EDC) (0.108 g, 0.562 mmol) and 4-(dimethylamino)pyridine (DMAP) (0.0077 g, 0.063 mmol). The mixture was stirred under argon at room temperature for 5 hours. The solvent was removed under vacuum and the residue was purified by silica gel column chromatography (hexane-ethyl acetate 1:1) to afford 0.24 g (0.31 mmol, 98% yield) of product (20) as a syrup: $^1$H NMR (CDCl$_3$, 200 MHz) δ 0.87 (t, 3H, J=6.3 Hz), 1.25 (bs, 24H), 1.46 (s, 9H), 1.93 (m, 2H), 2.30 (m, 2H), 2.49 (m, 2H), 2.80 (dd, 1H, J=16.6, 4.8 Hz), 2.93 (dd, 1H, J=16.6, 5.0 Hz), 4.24–4.33 (m, 2H), 4.48–4.54 (m, 2H), 4.67–4.72 (m, 1H), 5.97 (d, 1H), 7.29–7.43 (m, 5H), 7.62 (d, 2H, J=7.2 Hz), 7.76 (d, 2H, J=7.2 Hz), 9.59 (bs, 1H), 10.58 (bs, 1H).

EXAMPLE 21

Preparation of the compound of formula (I) where $X_1$=S, $X_2$=O, $R_1$=—(CH$_2$)$_{13}$CH$_3$,

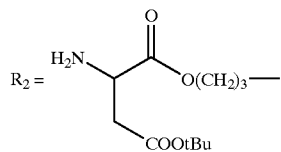

and $R_3=R_4=H$ [compound (21)]

Scheme 7

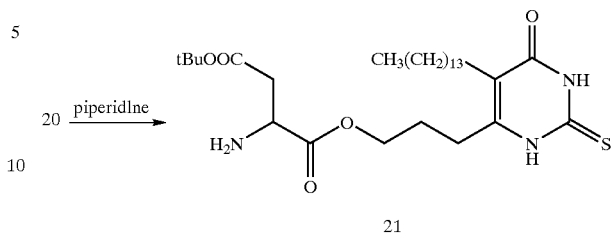

According to the above scheme 7 a solution of Fmoc-protected product (20) (0.120 g, 0.155 mmol) in anhydrous dichloromethane (5 ml) was treated with 0.020 g of piperidine (0.23 mmol). The mixture was stirred at room temperature for 30 minutes. The solvent was removed under vacuum and the residue was purified by silica gel column chromatography (hexane-ethyl acetate 3:7) to afford 0.040 g (0.072 mmol, 47% yield) of product (20) as a syrup: $^1$H NMR (CDCl$_3$, 200 MHz) δ 0.87 (t, 3H, J=6.6 Hz), 1.25 (bs, 24H), 1.46 (s, 9H), 1.94 (m, 2H), 2.33 (t, 2H, J=7.2 Hz), 2.56 (t, 2H, J=7.7 Hz), 2.76 (d, 2H, J=5.9 Hz), 3.94 (t, 1H, J=5.8 Hz), 4.21–4.30 (m, 2H).

EXAMPLE 22

Preparation of the compound of formula (I) where $X_1$=S, $X_2$=O, $R_1$=—(CH$_2$)$_{13}$CH$_3$,

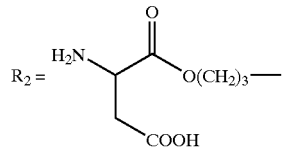

and $R_3=R_4=H$ [compound (22)]

Scheme 8

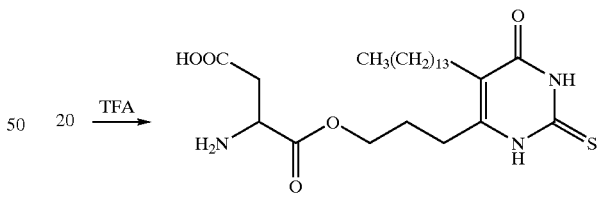

According to the above scheme 8 the tert-Butyl ester (21) (0.020 g, 0.040 mmol) was treated with 0.2 ml of a 1:1 mixture of trifluoroacetic acid and dichloromethane. The mixture was stirred at room temperature for 1 hour. The solvent was removed under vacuum and the residue was purified by silica gel column chromatography (acetone-methanol, variable ratios from 100:0 to 50:50) to afford 0.012 g (0.021 mmol, 54% yield) of product (20) as a syrup: $^1$H NMR (CD$_3$OD, 200 MHz) δ 0.89 (t, 3H, J=6.8 Hz), 1.29 (bs, 24H), 1.97 (m, 2H), 2.35 (m, 2H), 2.57 (m, 2H), 2.82 (m, 2H), 4.16–4.44 (m, 3H).

EXAMPLE 23

Preparation of the compound of formula (I) where $X_1=S$, $X_2=O$, $R_1=-(CH_2)_{13}CH_3$,

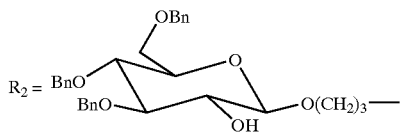

and $R_3=R_4=H$ [compound (23)]

Scheme 9

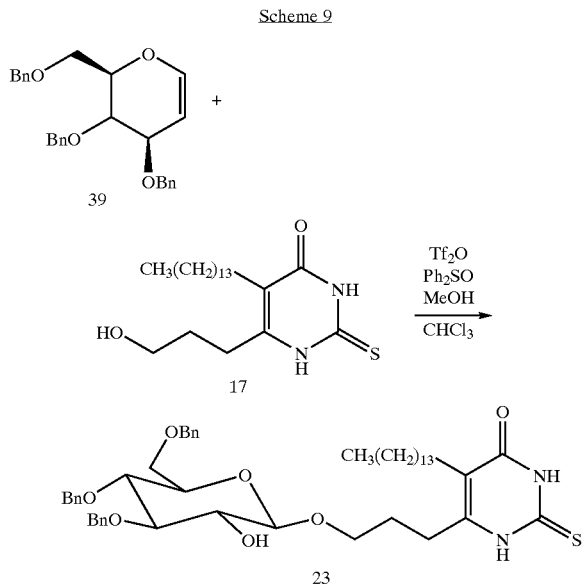

wherein Bn is benzyl.

Glucose derivative (23) was prepared following a general procedure for direct glycosilation of alcohols with glucal donor (39) (as reported in: V. Di Bussolo, Y.-J. Kim, D. Y. Gin *J. Am. Chem. Soc.* 1998, 120, 13515–13516), as reported above in scheme 9.

Triflouromethanesulfonic anhydride ($Tf_2O$) (0.030 ml, 0.18 mmol) was added to a solution of tri-O-benzil-D-glucal (39) (0.050 g, 0.12 mmol), diphenylsulfoxide (0.073 g, 0.36 mmol) and 2,4,6-tri-t-butylpyridine (0.104 g, 0.42 mmol) in dry chloroform (5 ml) (distilled over $P_2O_5$) at −40° C. The reaction mixture was stirred at this temperature for 1 hour. Methanol (0.005 ml, 0.12 mmol) and triethylamine (0.050 ml, 0.36 mmol) were added sequentially at −40° C. and the reaction mixture was stirred at this temperature for 30 minutes, then at 0° C. for 1 hour and at room temperature for 1 hour. A solution of alcohol derivative (17) (0.065 g, 0.17 mmol) in dry chloroform (4 ml) was added at 0° C., via cannula. Zinc chloride (0.24 ml, 1.0 M in diethyl ether, 0.24 mmol) was added at the same temperature, then the temperature was slowly warmed to room temperature and the reaction mixture stirred at this temperature for 12 hours. The reaction was diluted with chloroform (15 ml) and washed sequentially with saturated aqueous sodium bicarbonate solution (2×15 ml) and a saturated aqueous solution of sodium chloride (15 ml). The organic layer was dried ($Na_2SO_4$) and concentrated, the residue was purified by silica gel column chromatography (hexane-ethyl acetate 6:4) to afford product (23) (0.055 g, 0.067 mmol, 56% yield) as a colourless oil: $^1$H NMR ($CDCl_3$) δ 0.87 (t, 3H, J=6.3 Hz), 1.25 (bs, 24H), 1.88 (quintet, 2H, J=6.4 Hz), 2.44 (pseudo t, 2H, J=7.5 Hz), 2.65 (t, 2H, J=6.6 Hz), 3.70–3.66 (m, 8H), 4.47 (d, 1H, J=10.6 Hz), 4.52 (d, 1H, J=12.1 Hz), 4.65 (d, 1H, J=12.1 Hz), 4.80 (d, 1H, J=10.8 Hz), 4.86 (d, 1H, J=11.4 Hz), 4.92 (d, 1H, J=11.2 Hz), 5.12 (d, 1H, J=9.2 Hz), 7.09–7.35 (m, 15H), 9.61 (bs, 1H), 11.29 (bs, 1H); MS ($FAB^+$) m/z 815 $(M+H)^+$.

EXAMPLE 24

Preparation of the compound of formula (I) where $X_1=S$, $X_2=O$, $R_1=-(CH_2)_{13}CH_3$, $R_2$=ethyl, $R_3=-CH_2COOC_2H_5$, and $R_4=H$ [compound (24)]

Anhydrous $(NH_4)_2SO_4$ (0.0013 g, 0.011 mmol) and 1,1,1,3,3,3-hexamethyldisilazane (HMDS) (0.75 ml, 3.41 mmol) were added, under argon atmosphere, to compound (3) (0.05 g, 0.14 mmol). The resulting suspension was heated at 130° C. and stirred at this temperature for 6 hours. The mixture was then concentrated at room temperature under a flux of argon. Anhydrous THF (3 ml) was added, and the resulting solution was stirred at −45° C. Trimethylsilyl triflate (TMS triflate) (0.03 ml, 0.145 mmol) and ethyl bromoacetate (0.046 g, 0.027 mmol) were sequentially added and the mixture was stirred at −45° C. for 3 hours, then at room temperature for 1 hour. Saturated aqueous $NaHCO_3$ (3 ml) was added and THF was removed under vacuum. The residue was diluted with $H_2O$ (20 ml) and extracted with ethyl acetate (3×10 ml). The organic layer was dried with $Na_2SO_4$ anhydrous, and concentrated to dryness. The residue was purified by semi-preparative thin-layer column chromatography (hexane/ethyl acetate 7:3) to afford product (24) (0.010 g, 0.023 mmol, 16% yield) as a colourless oil: $^1$H NMR ($CDCl_3$, 200 MHz) δ 0.87 (t, 3H, J=6.6 Hz), 1.17 (t, 3H, J=7.2 Hz), 1.25–1.43 (m, 27H), 2.44 (pseudo t, 2H, J=7.2 Hz), 2.54 (t, 2H, J=7.5 Hz), 3.91 (s, 2H), 4.21 (q, 2H, J=7.3 Hz), 10.88 (bs, 1H); ); MS ($FAB^+$) m/z 439 $(M+H)^+$.

According to procedures analogues to those above reported, the following compounds of formula (I) were prepared:

compound (I) wherein $X_1=S$, $X_2=O$, $R_1=-(CH_2)_{13}CH_3$,

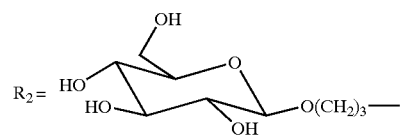

and $R_3=R_4=H$ [compound (25)];
compound (I) wherein $X_1=S$, $X_2=O$, $R_1=-(CH_2)_{13}CH_3$, $R_2=-(CH_2)_3Br$ and $R_3=R_4=H$ [compound (26)];
compound (I) wherein $X_1=S$, $X_2=O$, $R_1=-(CH_2)_{13}CH_3$,

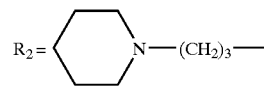

and $R_3=R_4=H$ [compound (27)];
compound (I) wherein $X_1=S$, $X_2=O$, $R_1=-(CH_2)_{13}CH_3$, $R_2=-(CH_2)_3N(C_2H_5)_3^+Br^-$ and $R_3=R_4=H$ [compound (28)];

CYTOTOXICITY TEST

The cytotoxicity of the compounds synthesized 1–28 was assessed using a human leukemia cell line called CCRF/CEM. The CCRF/CEM cells were cultured in a culture medium containing RPMI 1640 (90%), bovine fetal sera (10%) and interleukin-2 (100 U/ml). The cytotoxicity assay was performed on 104 CCRF/CEM cells seeded in 35 mm wells in 2 ml of culture medium. The cells were treated with the compounds under consideration for 72 hours and at the end of the period of exposure their number was counted and compared with that of control cells treated with $C_2$-ceramide in order to establish the percentage of growth inhibition. The concentration capable of inhibiting 50% of cell growth was calculated by non-linear regression of the experimental data as described in M. Macchia, N. Jannitti, G. B. Gervasi, R. Danesi, *J Med Chem,* (1996) 39 (7): 1352–1356.

The resulting values of $IC_{50}$ expression in $\mu M$ are given in the following table:

| Compound | $IC_{50}$ ($\mu M$) |
|---|---|
| controls | 31.6 |
| (3) | 1.7 |
| (4) | 6.3 |
| (6) | 0.97 |
| (9) | 13.2 |
| (10) | 8.7 |
| (11) | 20 |
| (12) | 29.1 |
| (13) | 20.7 |
| (14) | 15.6 |

What is claimed is:

1. A compound of general formula (I)

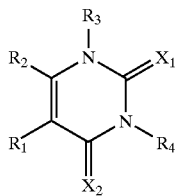

(I)

where $X_1$ and $X_2$ are selected between O and S;

$R_1$ and $R_2$ are selected between —$(CH_2)_{13}CH_3$ and alkyl or alkylene groups with from 2 to 6 carbon atoms, linear or branching, unsubstituted or substituted with one or more substituents selected among aromatic, primary, secondary and tertiary aminic, quaternary ammonium, carboxylic, hydroxylic, polyoxyalkyl and ethereal groups, amino acids, halogen atoms or glucose or a derivative thereof a saccharide moiety having the structure

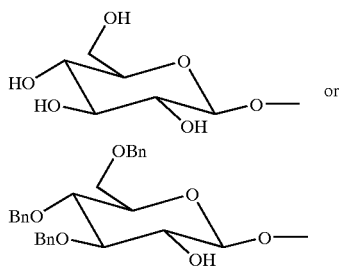

providing that between $R_1$ and $R_2$ only one is always —$(CH_2)_{13}CH_3$, $R_3$ and $R_4$ are selected between H and alkyl or alkylene groups with from 2 to 6 carbon atoms, linear or branching, unsubstituted or substituted with one or more substituents selected among aromatic, primary, secondary and tertiary aminic, quaternary ammonium, carboxylic, hydroxylic, polyoxyalkyl and ethereal groups, amino acids, halogen atoms or glucose or a derivative thereof.

2. A compound having the general formula (I)

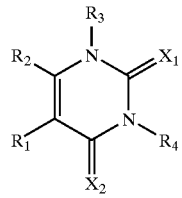

(I)

wherein:

$X_1$=S, $X_2$=O, $R_1$=ethyl, $R_2$=—$(CH_2)_{13}CH_3$, and $R_3$=$R_4$=H (compound 1);

$X_1$=$X_2$=O, $R_1$=ethyl, $R_2$=—$(CH_2)_{13}CH_3$, and $R_3$=$R_4$=H (compound 2);

$X_1$=S, $X_2$=O, $R_1$=—$(CH_2)_{13}CH_3$, $R_2$=ethyl, and $R_3$=$R_4$=H (compound 3);

$X_1$=$X_2$=O, $R_1$=—$(CH_2)_{13}CH_3$, $R_2$=ethyl, and $R_3$=$R_4$=H (compound 4);

$X_1$=S, $X_2$=O, $R_1$=—$(CH_2)_{13}CH_3$, $R_2$=n-propyl, and $R_3$=$R_4$=H (compound 5);

$X_1$=$X_2$=O, $R_1$=—$(CH_2)_{13}CH_3$, $R_2$=n-propyl, and $R_3$=$R_4$=H (compound 6);

$X_1$=S, $X_2$=O, $R_1$=—$(CH_2)_{13}CH_3$, $R_2$=n-butyl, and $R_3$=$R_4$=H (compound 7);

$X_1$=$X_2$=O, $R_1$=—$(CH_2)_{13}CH_3$, $R_2$=n-butyl, and $R_3$=$R_4$=H (compound 8);

$X_1$=S, $X_2$=O, $R_1$=—$(CH_2)_{13}CH_3$, $R_2$=i-butyl, and $R_3$=$R_4$=H (compound 9);

$X_1$=$X_2$=O, $R_1$=—$(CH_2)_{13}CH_3$, $R_2$=i-butyl, and $R_3$=$R_4$=H (compound 10);

$X_1$=S, $X_2$=O, $R_1$=—$(CH_2)_{13}CH_3$, $R_2$=neopentyl, and $R_3$=$R_4$=H (compound 11);

$X_1$=$X_2$=O, $R_1$=—$(CH_2)_{13}CH_3$, $R_2$=neopentyl, and $R_3$=$R_4$=H (compound 12);

$X_1$=S, $X_2$=O, $R_1$=—$(CH_2)_{13}CH_3$, $R_2$=2-phenyl-ethyl, and $R_3$=$R_4$=H (compound 13);

$X_1$=$X_2$=O, $R_1$=—$(CH_2)_{13}CH_3$, $R_2$=2-phenyl-ethyl, and $R_3$=$R_4$=H (compound 14);

$X_1$=S, $X_2$=O, $R_1$=—$(CH_2)_{13}CH_3$, $R_2$=—$(CH_2)_3NH_2$, and $R_3$=$R_4$=H (compound 15);

$X_1$=S, $X_2$=O, $R_1$=—$(CH_2)_{13}CH_3$, $R_2$=—$(CH_2)_3OSiPh_2t$-Bu, and $R_3$=$R_4$=H (compound 16);

$X_1$=S, $X_2$=O, $R_1$=—$(CH_2)_{13}CH_3$, $R_2$=—$(CH_2)_3OH$, and $R_3$=$R_4$=H (compound 17);

$X_1$=S, $X_2$=O, $R_1$=—$(CH_2)_{13}CH_3$, $R_2$=—$(CH_2)_3OC(O)CH_2NH$-Cbz, and $R_3$=$R_4$=H (compound 18);

$X_1$=S, $X_2$=O, $R_1$=—$(CH_2)_{13}CH_3$, $R_2$=—$(CH_2)_3OC(O)CH_2NH_2$, and $R_3$=$R_4$=H (compound 19);

$X_1$=S, $X_2$=O, $R_1$=—$(CH_2)_{13}CH_3$, $R_2$=

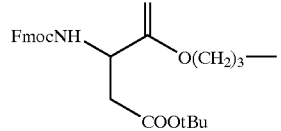

and $R_3$=$R_4$=H (compound 20);

19

$X_1=S$, $X_2=O$, $R_1=-(CH_2)_{13}CH_3$

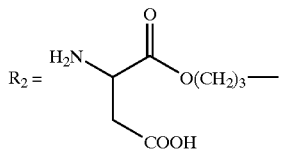

and $R_3=R_4=H$ (compound 21);
$X_1=S$, $X_2=O$, $R_1=-(CH_2)_{13}CH_3$

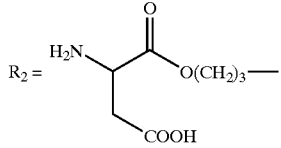

and $R_3=R_4=H$ (compound 22);
$X_1=S$, $X_2=O$, $R_1=-(CH_2)_{13}CH_3$

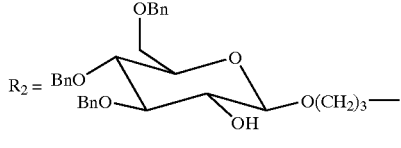

wherein Bn is benzyl and $R_3=R_4=H$ (compound 23);
$X_1=S$, $X_2=O$, $R_1=-(CH_2)_{13}CH_3$, $R_2$=ethyl, $R_3=-CH_2COOC_2H_5$, and $R_4=H$ (compound 24);

20

$X_1=S$, $X_2=O$, $R_1=-(CH_2)_{13}CH_3$

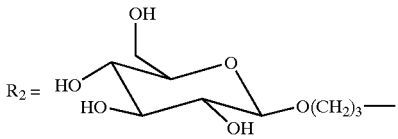

and $R_3=R_4=H$ (compound 25);
$X_1=S$, $X_2=O$, $R_1=-(CH_2)_{13}CH_3$, $R_2=-(CH_2)_3Br$, and $R_3=R_4=H$ (compound 26);
$X_1=S$, $X_2=O$, $R_1=-(CH_2)_{13}CH_3$

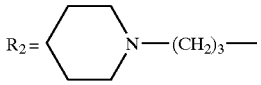

and $R_3=R_4=H$ (compound 27);
$X_1=S$, $X_2=O$, $R_1=-(CH_2)_{13}CH_3$, $R_2=-(CH_2)_3N(C_2H_5)_3$ $^+Br^-$, and $R_3=R_4=H$ (compound 28).

3. A compound of claim 2, wherein:
$X_1=S$, $X_2=O$, $R_1=-(CH_2)_{13}CH_3$, $R_2$=ethyl, and $R_3=R_4=H$ (compound 3);
$X_1=X_2=O$, $R_1=-(CH_2)_{13}CH_3$, $R_2$=ethyl, and $R_3=R_4=H$ (compound 4);
$X_1=X_2=O$, $R_1=-(CH_2)_{13}CH_3$, $R_2$=n-propyl, and $R_3=R_4=H$ (compound 6);
$X_1=X_2=O$, $R_1=-(CH_2)_{13}CH_3$, $R_2$=i-butyl, and $R_3=R_4=H$ (compound 10).

* * * * *